United States Patent
Thomas

(10) Patent No.: US 7,766,893 B2
(45) Date of Patent: Aug. 3, 2010

(54) TAPERED MULTI-CHAMBER BALLOON

(75) Inventor: Kory Thomas, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 387 days.

(21) Appl. No.: 11/296,793

(22) Filed: Dec. 7, 2005

(65) Prior Publication Data

US 2007/0129749 A1   Jun. 7, 2007

(51) Int. Cl.
*A61M 31/00* (2006.01)

(52) U.S. Cl. ............. 604/509; 604/99.02; 604/101.1; 606/194

(58) Field of Classification Search ........... 604/103.07, 604/96.01, 99.02, 99.04, 101.01, 101.05, 604/509, 99.01; 606/194
See application file for complete search history.

(56) References Cited

U.S. PATENT DOCUMENTS

| | | | |
|---|---|---|---|
| 388,510 A | 8/1888 | Terrell | |
| 550,238 A | 11/1895 | Allen, Jr. | |
| 3,504,662 A * | 4/1970 | Jones | 600/18 |
| 4,338,942 A | 7/1982 | Fogarty | 128/344 |
| 4,490,421 A | 12/1984 | Levy | |
| 4,546,759 A | 10/1985 | Solar | 128/1 |
| 4,581,017 A | 4/1986 | Sahota | 604/101 |
| 4,744,366 A | 5/1988 | Jang | 128/344 |
| 4,763,654 A * | 8/1988 | Jang | 606/195 |
| 4,906,244 A | 3/1990 | Pinchuk et al. | |
| 4,950,239 A | 8/1990 | Gahara et al. | |
| 4,958,634 A | 9/1990 | Jang | 606/194 |
| 4,994,033 A | 2/1991 | Shockey et al. | 604/101 |
| 5,002,532 A | 3/1991 | Gaiser et al. | 604/101 |
| 5,019,042 A | 5/1991 | Sahota | 604/101 |
| 5,176,619 A * | 1/1993 | Segalowitz | 600/18 |
| 5,250,069 A | 10/1993 | Nobuyoshi et al. | |
| 5,264,260 A | 11/1993 | Saab | |
| 5,270,086 A | 12/1993 | Hamlin | |
| 5,273,536 A | 12/1993 | Savas | 604/96 |
| 5,304,135 A | 4/1994 | Shonk | 604/101 |
| 5,308,323 A | 5/1994 | Sogawa et al. | 604/95 |
| 5,328,468 A | 7/1994 | Kaneko et al. | |

(Continued)

FOREIGN PATENT DOCUMENTS

EP    1512381    3/2005

(Continued)

OTHER PUBLICATIONS

International Search Report for PCT/US07/19836, which claims priority to U.S. Appl. No. 11/592,691.

(Continued)

*Primary Examiner*—Nicholas D Lucchesi
*Assistant Examiner*—Laura A Bouchelle
(74) *Attorney, Agent, or Firm*—Vidas, Arrett & Steinkraus

(57) ABSTRACT

A catheter for carotid artery dilatation that includes a multi-chamber balloon assembly mounted at the distal end of the elongated tube that has at least two tandem chambers. Each chamber communicates with a separate lumen and each separate lumen terminates at the proximal end at a lumen valve head. The chambers have an inflated configuration with a diameter that progressively tapers in a direction from proximal to distal, said taper extends substantially continuously from the proximal end of the balloon assembly to the distal end thereof.

12 Claims, 11 Drawing Sheets

U.S. PATENT DOCUMENTS

| | | | |
|---|---|---|---|
| 5,344,400 A | 9/1994 | Kaneko et al. | |
| 5,415,635 A | 5/1995 | Bagaoisan et al. | 604/96 |
| 5,500,180 A | 3/1996 | Anderson et al. | |
| 5,536,252 A | 7/1996 | Imran et al. | 604/101 |
| 5,556,383 A | 9/1996 | Wang et al. | |
| 5,632,762 A | 5/1997 | Myler | |
| 5,725,535 A * | 3/1998 | Hegde et al. | 606/108 |
| 5,749,890 A | 5/1998 | Shaknovich | |
| 5,797,877 A | 8/1998 | Hamilton et al. | |
| 5,833,657 A | 11/1998 | Reinhardt et al. | |
| 5,865,801 A | 2/1999 | Houser | 604/96 |
| 5,868,777 A | 2/1999 | Lam | |
| 5,922,021 A | 7/1999 | Jang | |
| 6,022,359 A | 2/2000 | Frantzen | 606/108 |
| 6,086,548 A | 6/2000 | Chaisson et al. | 600/585 |
| 6,123,721 A | 9/2000 | Jang | |
| 6,146,356 A | 11/2000 | Wang et al. | |
| 6,210,429 B1 | 4/2001 | Vardi et al. | |
| 6,235,053 B1 | 5/2001 | Jang | |
| 6,261,319 B1 | 7/2001 | Kveen et al. | |
| 6,270,522 B1 | 8/2001 | Simhambhatla et al. | |
| 6,334,870 B1 | 1/2002 | Ehr et al. | |
| 6,348,065 B1 | 2/2002 | Brown et al. | |
| 6,471,720 B1 | 10/2002 | Ehr et al. | |
| 6,478,816 B1 | 11/2002 | Kveen et al. | |
| 6,488,653 B1 * | 12/2002 | Lombardo | 604/103.06 |
| 6,524,302 B2 | 2/2003 | Kelley | 604/523 |
| 6,527,739 B1 | 3/2003 | Bigus et al. | 604/101.01 |
| 6,582,396 B1 | 6/2003 | Parodi | 604/101.04 |
| 6,746,479 B2 | 6/2004 | Ehr et al. | |
| 6,776,771 B2 | 8/2004 | Van Moortegem et al. | 604/101.01 |
| 6,818,014 B2 | 11/2004 | Brown et al. | |
| 6,835,203 B1 | 12/2004 | Vardi et al. | |
| 6,905,490 B2 | 6/2005 | Parodi | 604/509 |
| 6,966,889 B2 | 11/2005 | Saab | 604/96.01 |
| 2002/0116047 A1 | 8/2002 | Vardi et al. | |
| 2002/0165521 A1 | 11/2002 | Cioanta et al. | |
| 2002/0173840 A1 | 11/2002 | Brucker et al. | |
| 2002/0193873 A1 | 12/2002 | Brucker et al. | |
| 2003/0097169 A1 | 5/2003 | Brucker et al. | |
| 2003/0109909 A1 | 6/2003 | Ledesma et al. | 607/100 |
| 2003/0195606 A1 | 10/2003 | Davidson et al. | |
| 2004/0054362 A1 | 3/2004 | Lopath et al. | |
| 2004/0088007 A1 | 5/2004 | Eidenschink | |
| 2004/0138732 A1 | 7/2004 | Suhr et al. | |
| 2004/0147811 A1 | 7/2004 | Diederich et al. | 600/207 |
| 2004/0172121 A1 | 9/2004 | Eidenschink et al. | |
| 2005/0015108 A1 | 1/2005 | Williams et al. | |
| 2005/0075662 A1 | 4/2005 | Pedersen et al. | 606/194 |
| 2005/0119731 A1 | 6/2005 | Brucker et al. | |
| 2005/0149161 A1 | 7/2005 | Eidenschink et al. | |
| 2005/0154442 A1 | 7/2005 | Eidenschink et al. | |
| 2005/0177221 A1 | 8/2005 | Mustapha | |
| 2005/0192656 A1 | 9/2005 | Eidenschink | |
| 2005/0234499 A1 | 10/2005 | Olson et al. | 606/192 |
| 2005/0261722 A1 | 11/2005 | Crocker et al. | |
| 2006/0064064 A1 | 3/2006 | Jang | |
| 2006/0116748 A1 | 6/2006 | Kaplan et al. | |
| 2006/0265041 A1 | 11/2006 | Sanati et al. | |
| 2006/0287712 A1 | 12/2006 | Eidenschink | |
| 2007/0038283 A1 | 2/2007 | Mustapha | |
| 2007/0050016 A1 | 3/2007 | Gregorich et al. | |
| 2007/0067011 A1 | 3/2007 | Krolik et al. | |
| 2007/0208411 A1 | 9/2007 | Meyer et al. | |

FOREIGN PATENT DOCUMENTS

| | | |
|---|---|---|
| WO | WO 97/17101 | 5/1997 |
| WO | 99/36015 | 7/1999 |
| WO | 2005/041810 | 5/2005 |
| WO | WO 2005/084745 | 9/2005 |
| WO | 2006/085304 | 8/2006 |

OTHER PUBLICATIONS

International Search Report for PCT/US07/19837, which claims priority to U.S. Appl. No. 11/592,365.

U.S. Appl. No. 11/592,365, filed Nov. 3, 2006, Chalekian.

U.S. Appl. No. 11/592,691, filed Nov. 3, 2006, Chalekian.

* cited by examiner

TAPERED MULTI-CHAMBER BALLOON

BACKGROUND OF THE INVENTION

Catheters having multiple or segmented balloons mounted thereon are known for a variety of uses. Some of these catheters the balloons communicate with a single inflation lumen, in others the different balloons or segments have separate lumens. Multiple balloons may be mounted on the catheter in tandem, concentrically or asymmetrically.

Certain applications to which catheters are applied present special problems. For instance, carotid artery steno sis has been treated using catheters for coronary angioplasty and/or for peripheral angioplasty, but have characteristic problems that create a need for specifically designed catheters. Carotid artery stenosis often originates in two common vessel areas of treatable significance. Primarily stenosis occurs at the bifurcation of the common carotid artery (CCA) and internal carotid artery (ICA). Secondarily, stenosis occurs in the ICA somewhat distal to the CCA and ICA bifurcation where the vessel size is substantially smaller.

Typically, those lesions found at the bifurcation of the CCA and CA are focal in nature, consist of large amounts of calcium and have a very heterogeneous surface morphology. When treating this kind of lesion set, a physician typically will pre and/or post dilate the lesion with a balloon. The pre-dilatation allows for ease of placement of the stent and the post-dilatation ensures the stent fully apposes the vessel contouring the stent to better conform to vessel configuration so that there is a well defined conduit for increased blood flow. The lesions found at the bifurcation of the CCA and CA make up approximately 80% of the world wide procedures that are treated with carotid artery stents. However, it would be useful if lesions in the internal carotid artery distal to the CCA and ICA bifurcation could also be treated at the same time with the same balloon catheter.

Documents describing some catheter systems and techniques for carotid artery surgery include U.S. Pat. No. 6,086,548 (Chaisson et al); U.S. Pat. No. 6,582,396 (Parodi); and U.S. Pat. No. 6,905,490 (Parodi).

SUMMARY OF THE INVENTION

The present invention pertains to a tapered multi-chamber balloon catheter particularly suited to carotid artery stenosis. The catheter includes an interventional balloon with two or more chambered compartments. The compartments are each tapered so that the overall inflated diameter range allows for dilatation at an artery bifurcation and/or within an artery distal to the bifurcation where the vessel size has substantially reduced.

In some embodiments the catheter is provided with a valve that provides for successive inflation of the balloon compartments in a distal to proximal fashion. These embodiments allow the physician to pre- and/or post dilate a lesion set within a tapering vessel of distally small to proximally larger diameters such as found mostly at the CCA and ICA bifurcation. In most instances this system will serve as a post dilatation balloon working extremely well with deployed tapered and/or self-tapering stents. The chambered system allows the physician to regulate the diameter size of the balloon to fit the vessel appropriately as it tapers.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The invention is illustrated in the Figures for an embodiment of the invention adapted for treatment of lesions located at a bifurcation between common carotid artery 15 (CCA) and internal carotid artery 16 (ICA), and/or within the ICA above the bifurcation.

Figure 1:
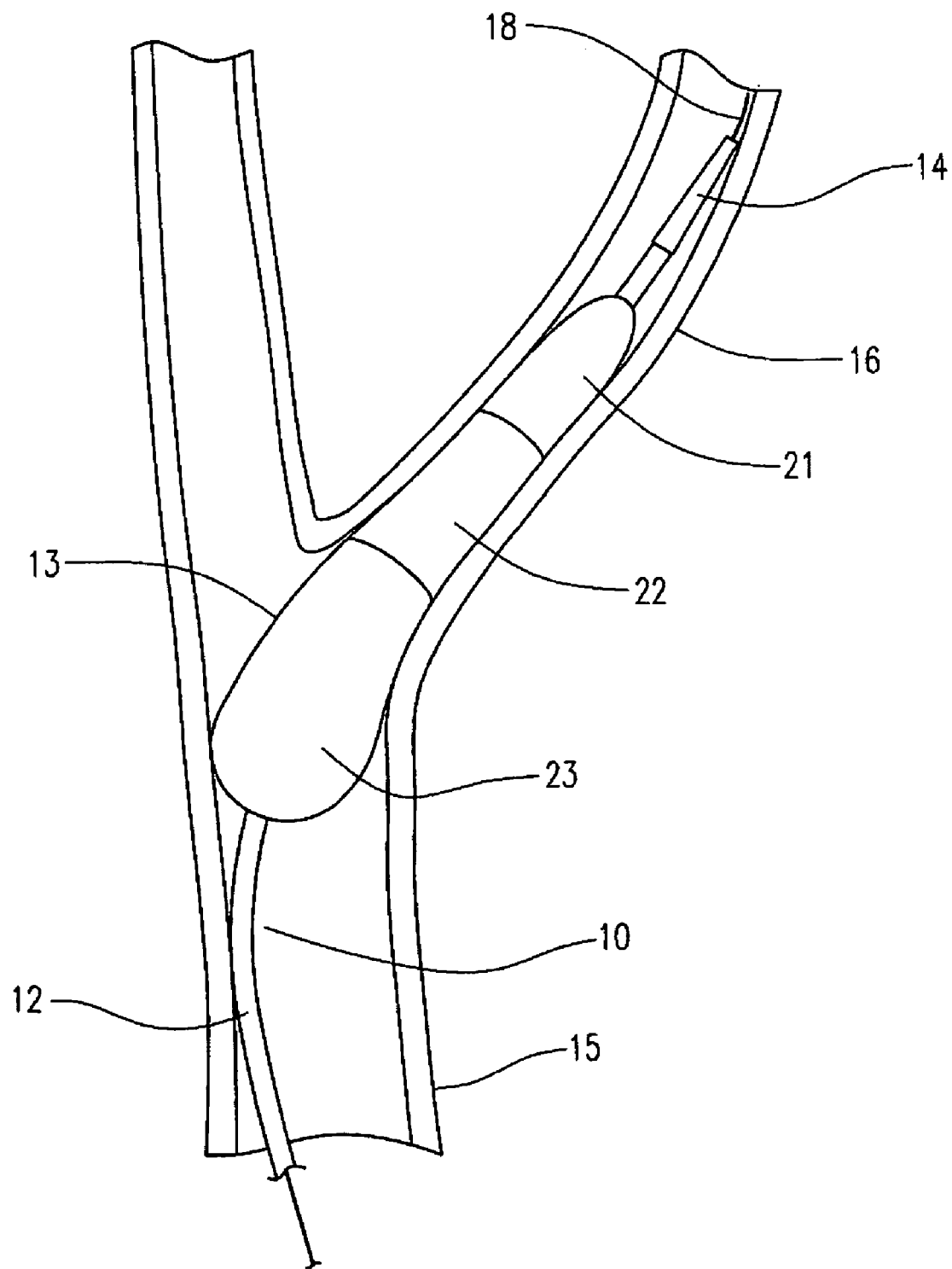
FIG. 1 is a schematic sectional view of a catheter located at a CCA-ICA bifurcation, with a tapered balloon of the invention in inflated state crossing the bifurcation.

Referring to FIG. 1, a catheter 10 is shown which includes a shaft 12, balloon 13 and distal end 14 is located at a bifurcation between common carotid artery 15 (CCA) and internal carotid artery 16 (ICA), the catheter shaft and balloon extend into internal carotid artery 16. Balloon 13 has three chambers 21, 22 and 23.

Catheter 10 is shown as an over-the-wire catheter that is deployed along a guide wire 18, but it should be understood that other catheter configurations, for instance rapid exchange catheter configurations may be employed without departing from the invention hereof.

Figure 2:
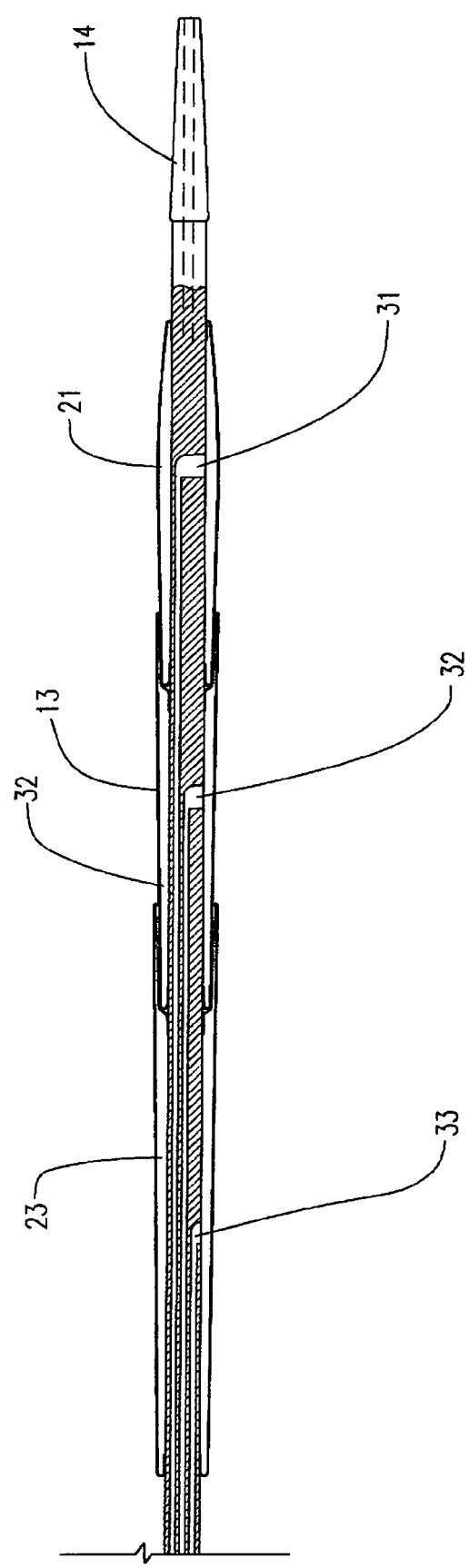
FIG. 2 is a longitudinal sectional view of the distal end of a catheter of the invention with the balloon in deflated state.

In FIG. 2 the distal end of catheter 10 is shown with the balloon 13 in deflated condition. Separate inflation lumens 31, 32, 33 are provided in shaft 12 which open respectively into the chambers 21, 22 and 23.

Figure 3:
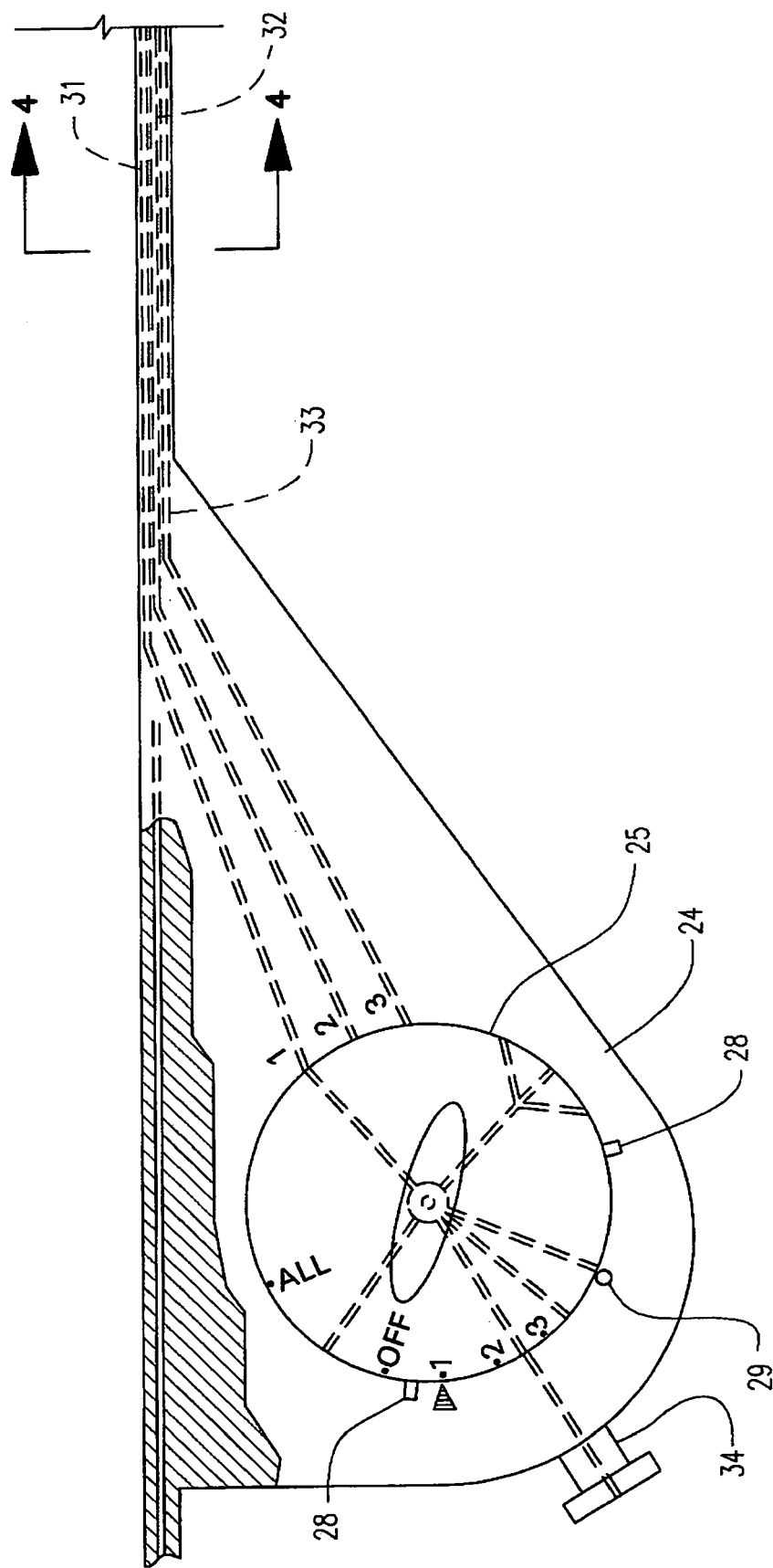
FIG. 3 is a schematic sectional view of the proximal end of the catheter with the control valve in the first inflation position.
Figure 4:
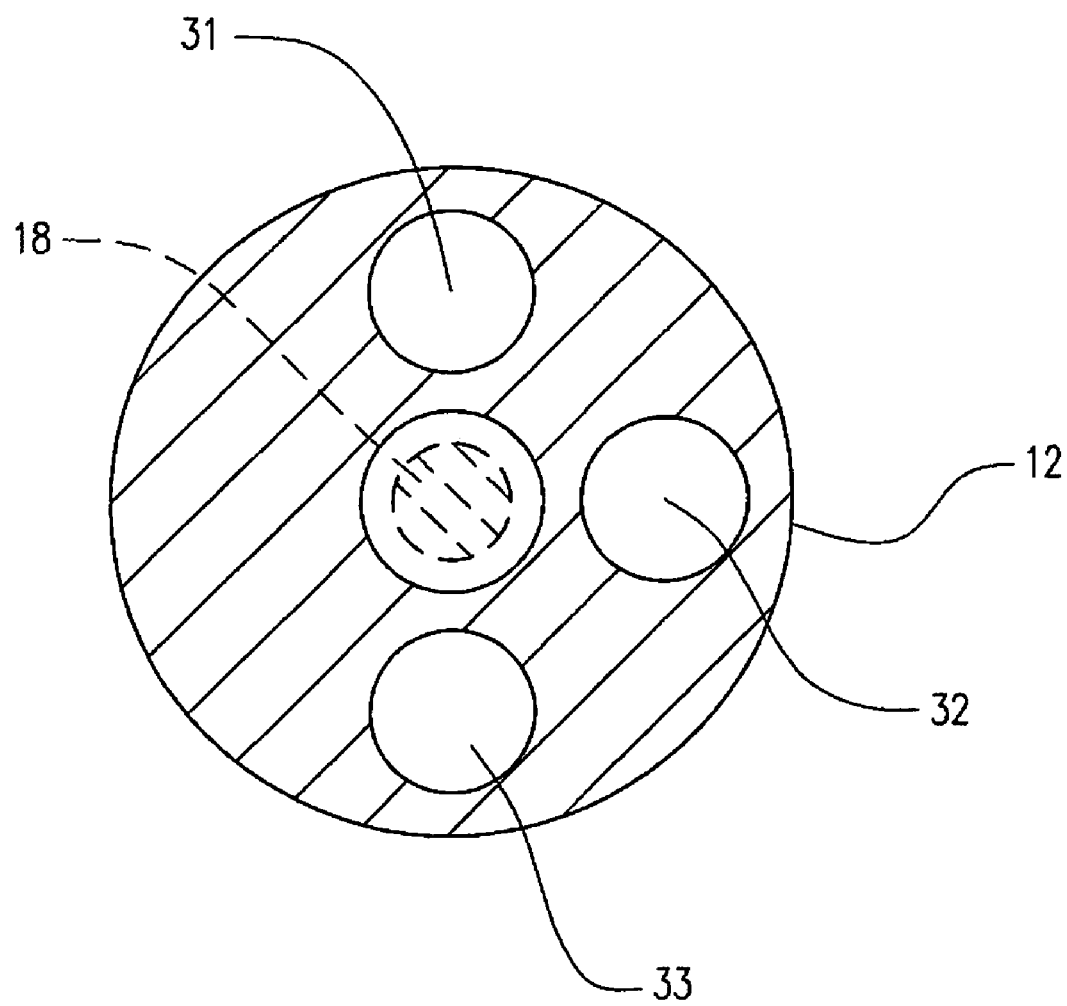
FIG. 4 is a cross sectional view taken at 4-4 of FIG. 3.

Referring to FIG. 3, at the proximal end of the system the control valve body is suitably designed to inflate each chamber sequentially in an incremental mode by way of a control valve 24 having a selection knob 25 thereon. In the incremental inflation mode the operation inflates chambers 21, 22, and 23 in that order to coordinate the distal to proximal inflation of the three balloon chambers.

Figure 6:
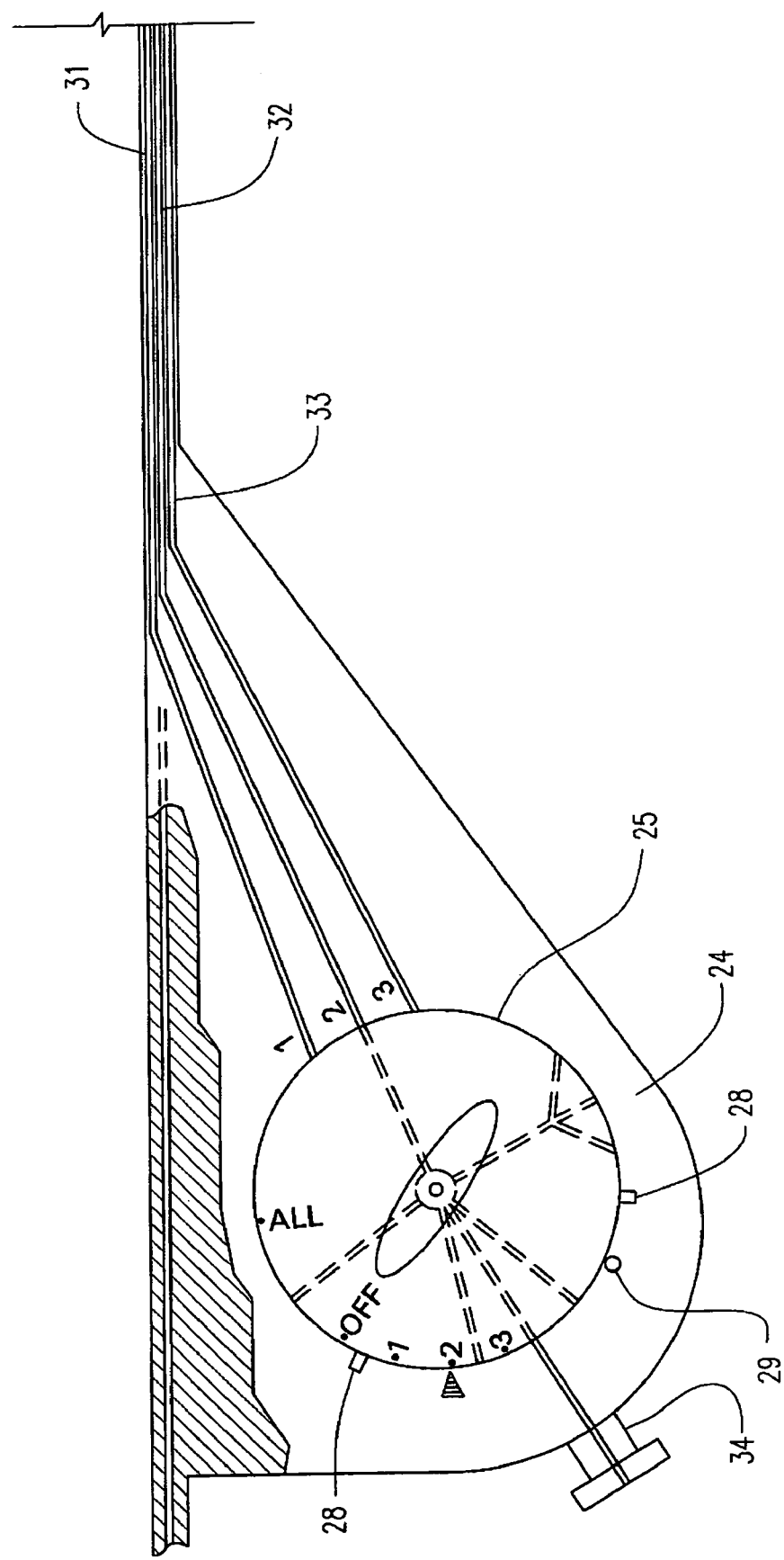
FIG. 6 is a view as in FIG. 3, but with the control valve in the second inflation position.
Figure 8:
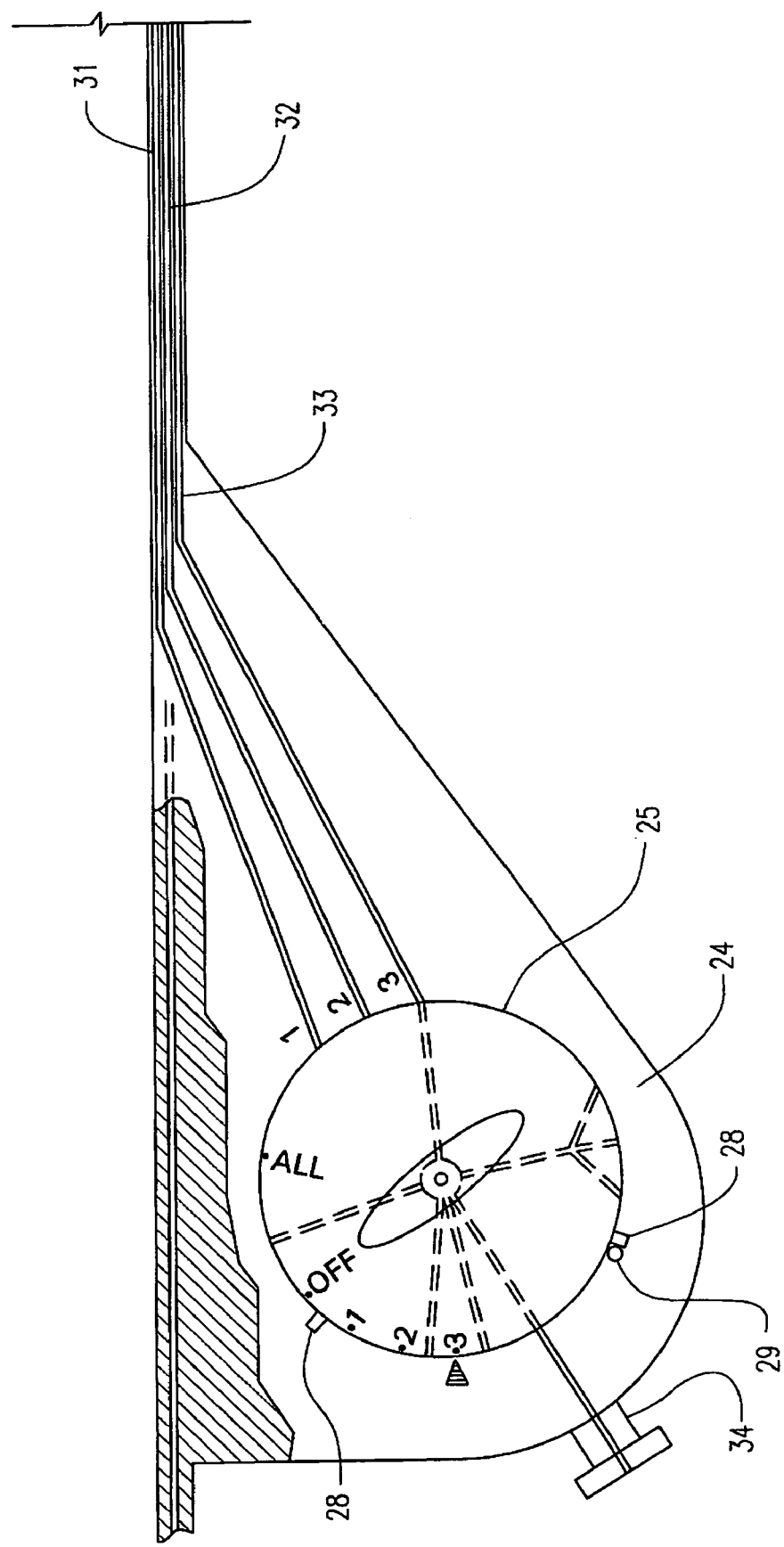
FIG. 8 is a view as in FIG. 3, but with the control valve in the third inflation position.

FIGS. 3, 6 and 8 depict various selection knob positions that are provided for the operator. A single inflation port 34 is provided for use with all three chambers. An incremental inflation sequence is desirably employed, so that the ICA is occluded distally first (FIG. 3) by rotating the selection knob 25 to position 1; the intermediate chamber 22 is inflated next by rotating the selection knob 25 further to position 2 (FIG. 6); and the largest chamber 23 is inflated by rotating the selection knob 25 to position 3 (FIG. 8). By inflating in sequence the most distally engagable surface of the ICA is encountered first and engagement therewith serves to secure the catheter against backing out of ICA when the balloon is employed to dilate a lesion more proximally in the ICA or at the ICA-CCA bifurcation. Also the chambered and tapered configuration of the balloon allows for most necessary dilations to be performed without inflation of all three chambers.

Figure 10:
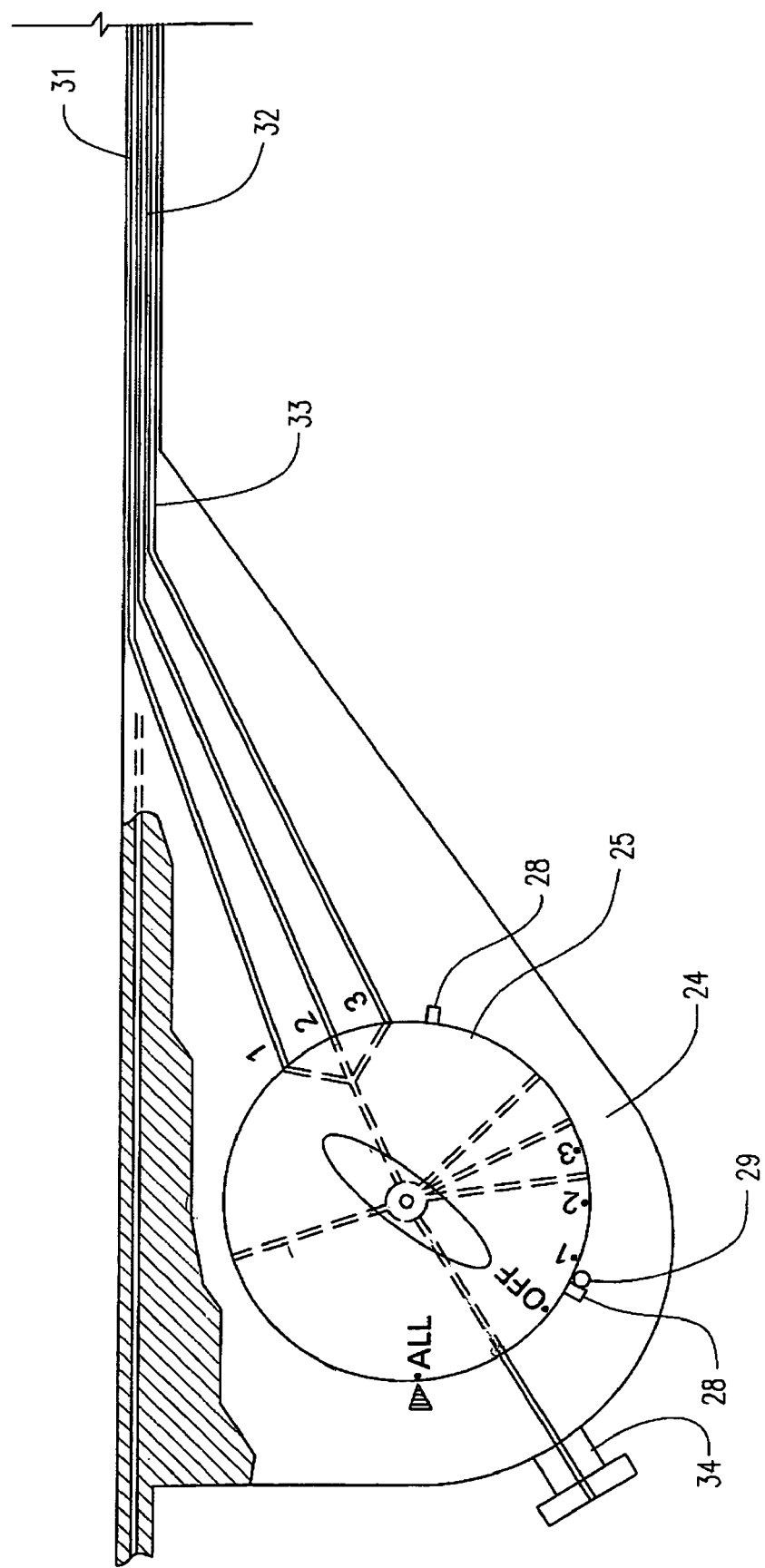
FIG. 10 is a view as in FIG. 3 with the control valve in the "all" position.

Optionally, a fourth position, the "all" position depicted in FIG. 10, is also provided wherein all three chambers may be inflated at the same time. Safety stops 28, which engage post 29 to limit rotation of the selection knob, may be provided on the selection knob to prevent the user from turning the knob to make an unintended lumen connection with port 34.

Figure 11:
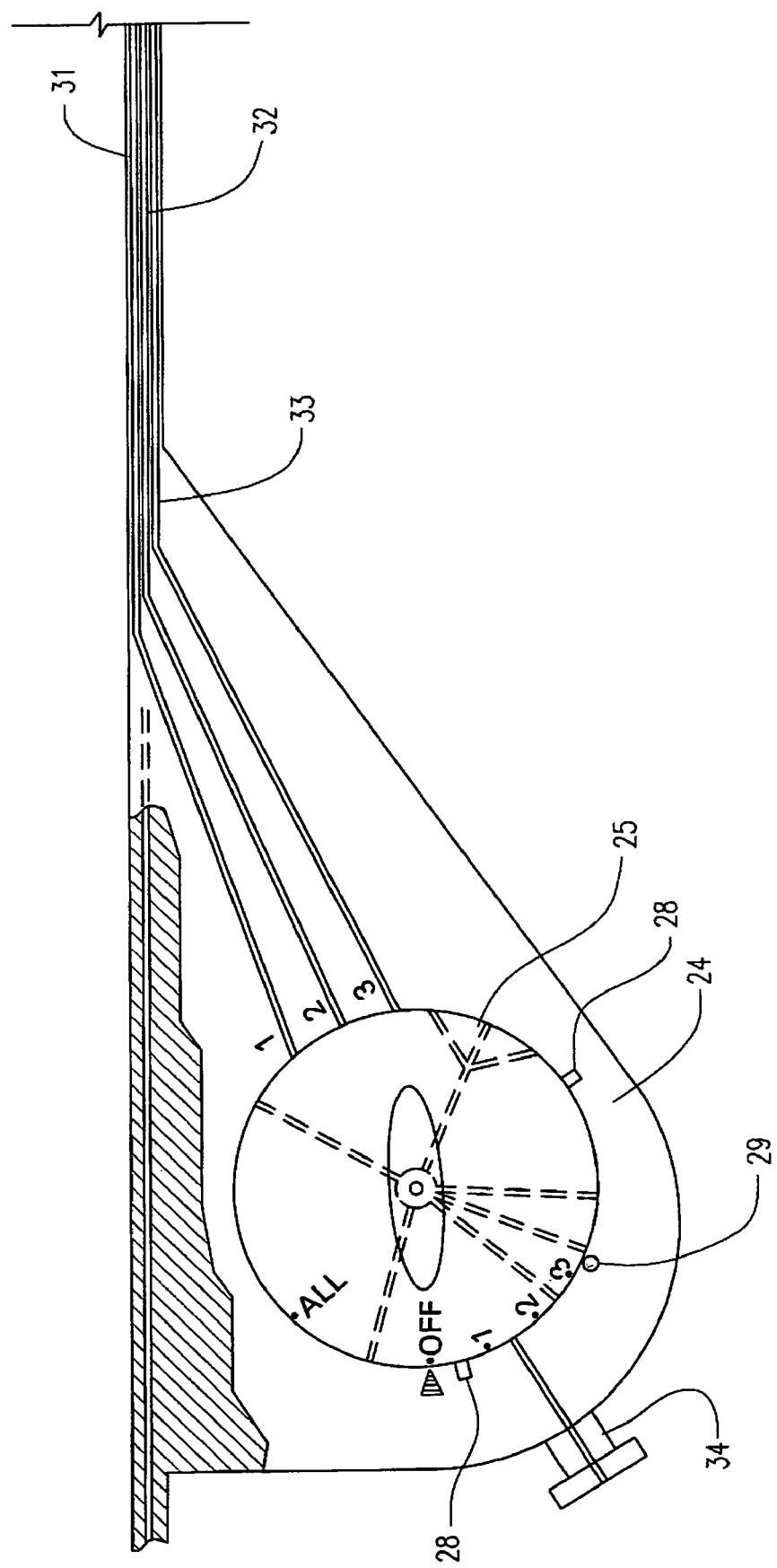
FIG. 11 is a view as in FIG. 3 with the control valve in the "off" position.

FIG. 11 illustrates an intermediate position "off" of the valve where no lumen connection is provided. Suitably a procedure is initiated from this position by rotating the valve knob clockwise or counterclockwise For an application at a CCA/ICA bifurcation, the taper (taken at nominal inflation of about 2 atm) suitably ranges in diameter from 4 mm at the most distal end of the balloon to 10 mm at the most proximal end. The catheter shaft may have a size of about 5 F. Each chamber may have a length in the range of from about 0.75 to about 1.75 cm, with a total length of the balloon assembly being in the range of about 3.5-4.5 cm.

Figure 5:
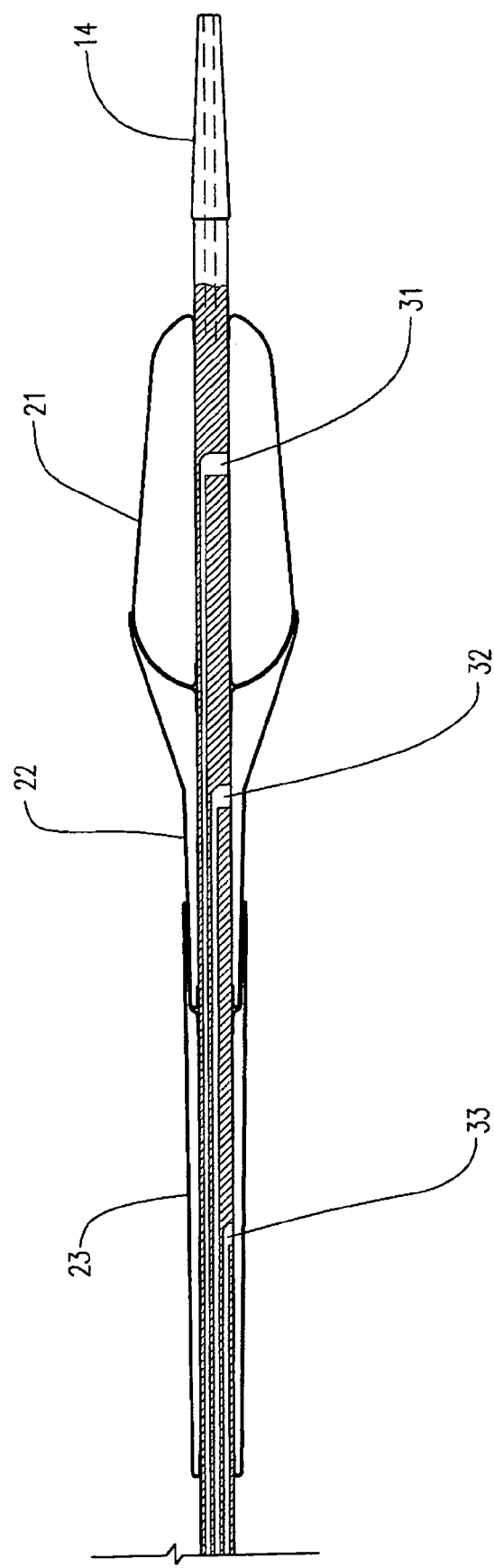
FIG. 5 is a view as in FIG. 2, but with the first chamber inflated.
Figure 7:
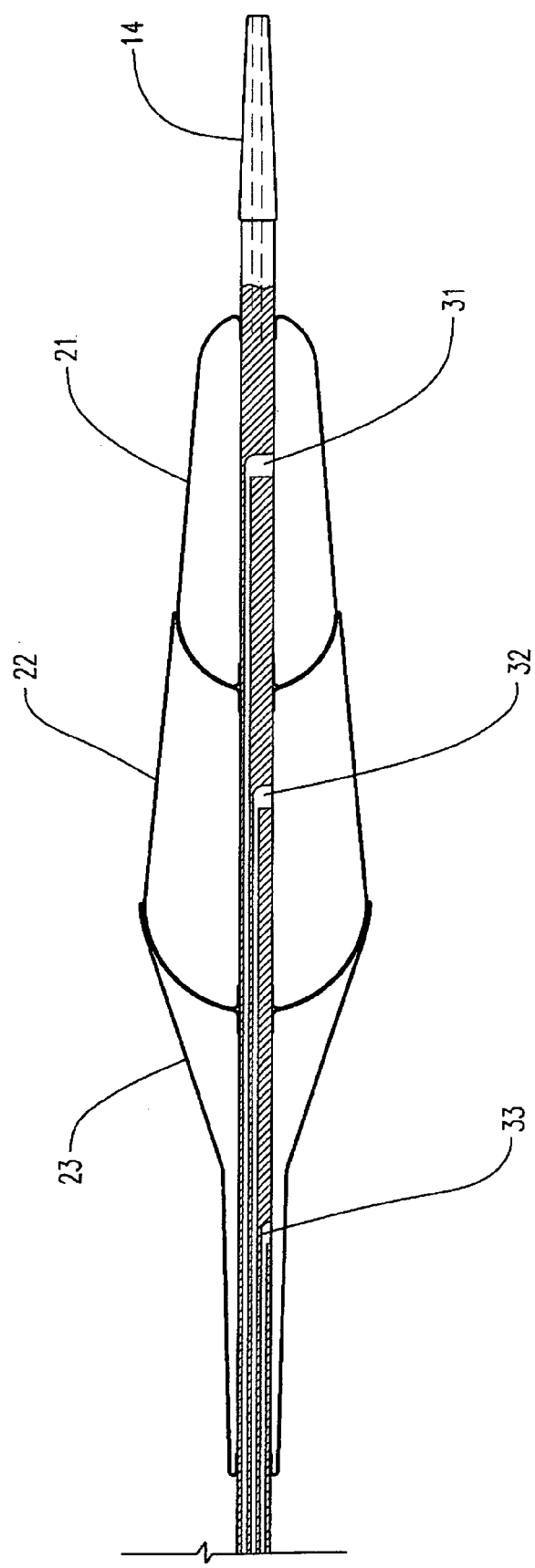
FIG. 7 is a view as in FIG. 2, but with the first and second chambers both inflated.
Figure 9:
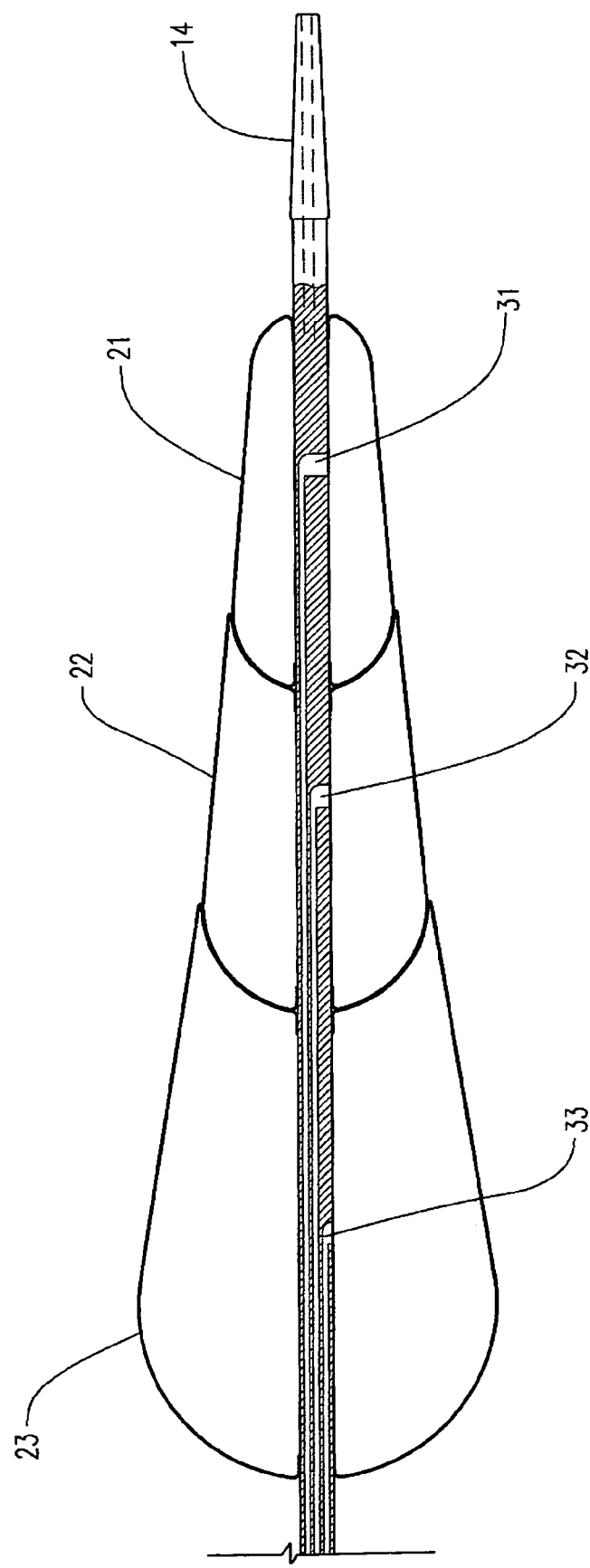
FIG. 9 is a view as in FIG. 2, but with all chambers inflated.

Referring to FIGS. 5, 7 and 9, the chamber sizes of balloon 13 are selected to provide substantially the entire range of dilatation sizes in progressively increasing diameter range that can be encountered in this artery system. For instance, chamber 21, which is the most distal chamber on the shaft, suitably may have a diameter range of 4-6 mm and a length of approximately 1.25-1.75 cm. In incremental inflation mode chamber 21 will always inflate first as depicted in FIG. 5. This chamber will ensure that no matter how large/or small the vessel is, it will inflate to the typically smallest diameter found in carotid arteries. In some instances, this portion of the system may be the only portion inflated to pre and/or post dilate the lesion as it may be used with short and/or focal lesions.

Chamber 22 is the middle chamber of balloon 13. Chamber 22 suitably may have a diameter range of 6-8 mm and a length of approximately 1.25-1.50 cm. Also suitably, the total length of chambers 21 and 22 will be about 30 mm, which represents approximately 75% of the lesions found in the carotids today. As shown in FIG. 7, in the incremental mode of inflation this chamber serves as the next chamber that will inflate after the chamber 21 has been inflated and the selection knob is moved to the second position. Inflation of chamber 22 will continue the dilatation of the vessel in the wider more proximal region of the ICA. Chamber 21 remains inflated when the valve is moved from the first to the second position.

Chamber 23 is the most proximal balloon on the shaft. Suitably chamber 23 may have a diameter range of 8-10 mm and a length of approximately 1 cm. This is the final chamber that is inflated in incremental inflation mode. Suitably the total system has a length of about 4 cm, which will provide appropriate coverage of 100% of the lesion sets found at the carotid bifurcation. Chambers 21 and 22 remain inflated when the valve is moved from the second to the third position.

While the invention has been described for a three-chambered balloon assembly, it should be understood that in some embodiments the invention the balloon assembly may have only two chambers and that in other embodiments more than three chambers may be employed.

Cylindrical tandem balloons, and techniques for mounting such balloons on catheters, are described in U.S. Pat. No. 4,763,654 (Jang). The same or similar techniques may be employed to mount the tapered multi-chambered balloons of the invention on catheters.

The balloon chambers may be formed of any polymer material having physical properties suitable for medical device dilatation or stent placement balloons. The polymers may be homopolymers, random copolymers, block copolymers or alternating copolymers. As used herein, the term copolymer refers to any polymer formed from more than one monomer. Blends of more than one polymer may also be employed or a mixture of a polymer and a modifier such as a plasticizer may be employed.

The balloon chambers may be formed of a single layer or of multiple layers of the same or different polymers or polymer blends. Reinforcing fibers may be provided on a macroscopic scale as a weave, braid or the like of the fiber, optionally entrained in a polymer matrix or as over the balloon, or on a microscopic scale as oriented fibers that are produced by phase separation from a blend during extrusion.

Examples of polymers that may be used to form the balloon chambers include polyesters such as polyethyleneterephthalate (PET), polybutylene terephthalate (PBT), polyethylene terephthalate/isophthalate copolymers and polyethylene naphthalate (PEN), polyethylene terephthalate/naphthalate copolymers; polyamides including nylon 12, nylon 11, nylon 10, nylon 610, nylon 6 and nylon 66; polyurethanes; block copolymers incorporating a polyester, polyamide, polyurethane and/or polyether segment; polycarbonates including polyesterpolycarbonates; any copolymers thereof; or blends comprising such polymers. Specific examples include polyamide/polyether/polyester block copolymers such as PEBAX® resins, in particular PEBAX 6333, 7033 and 7233, polyester/polyether block copolymers such as ARNITEL® EM 740 from DSM Engineering Plastics and polyurethanes such as ISOPLAST® 301 and PELLETHANE® 2363-75D from Dow Chemical Company.

Suitably the balloon distension profile is semi-compliant, nominally providing distension from about 2 atm to burst of about 10-25%. Polymers that can be employed to provide such a distension profile include the PEBAX®, ARNITEL® and PELLETHANE® resins previously mentioned.

In some embodiments of the invention the balloon material is the same for each chamber. In other embodiments the balloon material may be different from one chamber to the next. This may be desirable if it is desired to operate the catheter in a mode that provides different inflation pressures to the different chambers. Use of different inflation pressures between the chambers may be desirable, for instance because at a given inflation pressure, the force applied per unit of balloon area decreases. To counter this effect in the tapered multi-chamber balloon system of the present invention the balloon pressure may be increased as the inflation is successively incremented from the smallest to the largest chamber. The valve design accommodates such an operating mode since each inflated chamber is successively isolated from the pressure source once the next chamber is selected, when the incremental inflation mode is employed.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of dilating a carotid artery near a bifurcation between a common carotid artery (CCA) and internal carotid artery, the method comprising
   deploying a balloon catheter having proximal and distal ends and a plurality of lumens therethrough through the common carotid artery and into the internal carotid artery, wherein
      the catheter comprises a multi-chamber balloon assembly mounted at the distal end of the elongated tube comprising at least two tandem chambers, each chamber communicating with a separate lumen and each separate lumen terminating at the proximal end at a lumen valve head, and each chamber has an inflated configuration with a diameter that progressively tapers in a direction from proximal to distal, said taper extending substantially continuously from the proximal end of the balloon assembly to the distal end thereof,
   so that balloon assembly most proximal chamber of the balloon assembly crosses the bifurcation between the common carotid artery and the internal carotid artery, and
   inflating the chambers sequentially from the most distal chamber and then proceeding proximally until the desired dilation has been achieved.

2. A method as in claim 1 wherein the multi-chamber balloon assembly has at least three tandem chambers.

3. A method as in claim 2 wherein the dilatation is completed without inflation of at least the most proximal chamber of the balloon assembly.

4. A method as in claim 1 wherein the multi-chamber balloon assembly has three tandem chambers and each chamber has a length in the range of from about 0.75 to about 1.75 cm.

5. A method as in claim 4 wherein the balloon assembly tapers from a greatest diameter of about 10 mm at the proximal end of the most proximal chamber to a least diameter of about 4 mm at the distal end of the most distal chamber.

6. A method as in claim 1 wherein the balloon has a semi-compliant inflation profile.

7. A method of dilating a carotid artery near a bifurcation between a common carotid artery (CCA) and internal carotid artery, the method comprising
   deploying a balloon catheter having proximal and distal ends and a plurality of lumens therethrough through the common carotid artery and into the internal carotid artery, wherein
      the catheter comprises a multi-chamber balloon assembly mounted at the distal end of the elongated tube comprising at least two tandem chambers, each chamber communicating with a separate lumen and each separate lumen terminating at the proximal end at a lumen valve head, and each chamber has an inflated configuration with a diameter that progressively tapers in a direction from proximal to distal, said taper extending from the proximal end of the balloon assembly to the distal end thereof,
   so that the most proximal chamber of the balloon assembly crosses the bifurcation between the common carotid artery and the internal carotid artery, and
   inflating the chambers sequentially from the most distal chamber and then proceeding proximally until the desired dilation has been achieved.

8. A method as in claim 7 wherein the multi-chamber balloon assembly has at least three tandem chambers.

9. A method as in claim 8 wherein the dilatation is completed without inflation of at least the most proximal chamber of the balloon assembly.

10. A method as in claim 7 wherein the multi-chamber balloon assembly has three tandem chambers and each chamber has a length in the range of from about 0.75 to about 1.75 cm.

11. A method as in claim 10 wherein the balloon assembly tapers from a greatest diameter of about 10 mm at the proximal end of the most proximal chamber to a least diameter of about 4 mm at the distal end of the most distal chamber.

12. A method as in claim 7 wherein the balloon has a semi-compliant inflation profile.

* * * * *